US00PP22914P2

(12) United States Plant Patent
Egger

(10) Patent No.: US PP22,914 P2
(45) Date of Patent: Jul. 31, 2012

(54) ***HEUCHERA* PLANT NAMED 'BLACKBERRY CRISP'**

(50) Latin Name: ***Heuchera* spp.**
Varietal Denomination: Blackberry Crisp

(75) Inventor: Janet Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 64 days.

(21) Appl. No.: 12/930,839

(22) Filed: Jan. 19, 2011

(51) Int. Cl.
*A01H 5/00* (2006.01)

(52) U.S. Cl. ..... Plt./440

(58) Field of Classification Search ..... Plt./440
See application file for complete search history.

*Primary Examiner* — June Hwu

(74) *Attorney, Agent, or Firm* — Jondle & Associates, P.C.

(57) ABSTRACT

A new and distinct *Heuchera* plant substantially as shown and described, characterized by ruffled leaves, deep purple spring leaf color, glossy burgundy summer leaves, medium plant size, and excellent vigor.

1 Drawing Sheet

Botanical denomination: *Heuchera* spp.

Variety designation: 'Blackberry Crisp'.

The present invention relates to a new and distinct cultivar of *Heuchera* and given the cultivar name of 'Blackberry Crisp'. *Heuchera* is in the family Saxifragaceae. *Heuchera* 'Blackberry Crisp' originated from a planned cross between *Heuchera* 671-8, proprietary unreleased plant, as the seed parent, and *Heuchera* 816-8, a proprietary unreleased plant, as the pollen parent. Compared to the seed parent, *Heuchera* 671-8, the new cultivar has dark purple leaves rather than brown. Compared to the pollen parent, *Heuchera* 816-8, the new cultivar has leaves that are more ruffled.

Compared to *Heuchera* 'Purple Petticoats' (an unpatented plant), the new cultivar has a smaller tighter habit, shorter flowers, leaves with sharper ruffles, and darker purple foliage that holds its color all summer.

This new *Heuchera* is distinguished by:

1. ruffled leaves,
2. deep purple spring leaf color,
3. glossy burgundy summer leaves,
4. medium plant size, and
5. excellent vigor.

This new cultivar has been reproduced only by asexual propagation (cuttings and tissue culture). Each of the progeny exhibits identical characteristics to the original plant. Asexual propagation by stem cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one year old *Heuchera* 'Blackberry Crisp' in bloom, growing in the garden in May in Canby, Oreg.

FIG. 2 shows a one year old *Heuchera* 'Blackberry Crisp' in bloom in September in the trial field in Canby, Oreg.

DETAILED PLANT DESCRIPTION

The following is a detailed description of the new *Heuchera* cultivar based on observations of two-year-old specimens grown in 2 gallon containers outdoors in full sun in April in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette, herbaceous perennial.
*Hardiness*.—USDA Zone 4 to 9.
*Size*.—17 cm tall from top of the foliage to the ground and 40 cm wide.
*Habit*.—Mounding.
*Vigor*.—Excellent.
*Roots*.—Fibrous, freely branching, fine, and white in color; roots develop easily from cuttings.

Leaf:

*Type*.—Simple.
*Arrangement*.—Basal.
*Shape*.—Ovate.
*Lobing/division*.—5 main lobes, with 2 to 3 secondary lobes.
*Venation*.—Palmate.
*Margins*.—Crisped.
*Apex*.—Mucronulate.
*Base*.—Cordate, lobes overlapping slightly at the base.
*Blade size*.—Grows to 8.5 cm long and 8 cm wide.
*Surface texture*.—Both sides glandular.
*Petiole description*.—Grows to 13.5 cm long and 3 mm wide, glandular hairs, Greyed Purple 187B.
*Leaf color*.—Spring, top and bottom side, Purple N79A and Violet Blue N92A with interveinal highlights of Purple N79A; summer topside Greyed Purple N186A with interveinal veil Purple N79C and bottom side Greyed Purple N186A.

Inflorescence:

*Size*.—Grows to 6 cm wide and 24 cm long.

*Type*.—Thyrse.

*Number of flowers per thyrse*.—About 90 per thyrse.

*Number of thyrse*.—About 10 in first spring bloom.

*Peduncle*.—Grows to 28 cm tall and 5 mm wide at base, Greyed Purple N187A, glandular hairs, with about 2 petiolate leaves (ovate, blades grow to 5.5 cm long and 5 cm wide, 5 lobed with the terminal lobe the longest, margin undulate and deeply crenate, color the same as the leaves).

*Pedicel*.—Variable in size, with glandular hairs, Greyed Purple N187A.

*Bloom period*.—Late May to June with sporadic rebloom in Canby, Oreg.

Flower bud:

*Size*.—3 mm wide and 5 mm long.

*Description*.—Glandular puberulent, ovoid.

*Color*.—top ⅓ Yellow White 158B, bottom ⅔ Red Purple 70C.

Flower:

*Type*.—Perfect.

*Shape*.—Campanulate.

*Size*.—5 mm long and 4 mm wide.

*Petal description*.—5 in number, 2 mm long, spatulate with a clawed base, reflexed, tip acute, margin entire, glandular on top and bottom side, White NN155C on top side and White N155B on the bottom side.

*Calyx description*.—5 mm long and 4 mm wide, with 5 lobes, divided ½ way to the base, glandular hairs on both sides, tip obtuse, margin entire, both sides White N155B on top ⅔, Red Purple 70D on bottom ⅓.

*Stamen description*.—5 in number, 1.5 mm long, filaments White NN155D, anthers Greyed Orange 177A, no pollen, male sterile.

*Pistil description*.—One central two beaked pistil, 3 mm long, ovary 1 mm long and Yellow Green 152C, style 2 mm long , White NN155B.

*Fragrance*.—None.

*Lastingness*.—Each thyrse blooms for about 2 weeks on the plant.

Fruit:

*Type*.—Two beaked capsule.

*Size*.—7 mm deep by 2 mm wide.

*Fertility*.—Good.

*Color*.—Greyed Brown 199A.

Seed:

*Shape*.—Linear.

*Size*.—2 mm long.

*Color*.—Black, RHS 202A.

Disease and pest tolerance: No known resistances. Excellent disease tolerance to powdery mildew and *Heuchera* rust. All *Heuchera* are susceptible to root weevils.

I claim:

1. A new and distinct *Heuchera* plant as herein illustrated and described.

* * * * *

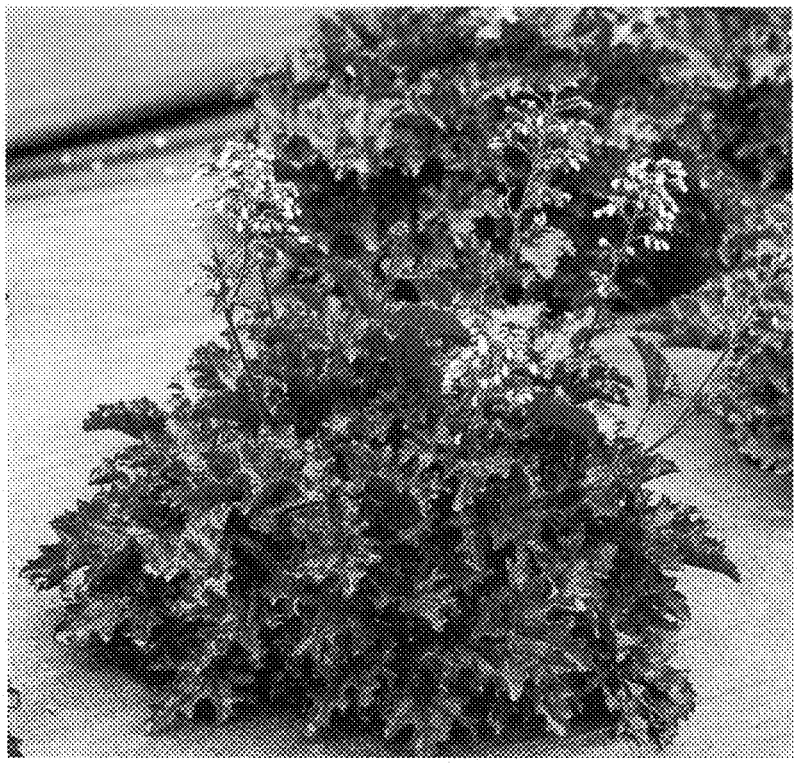

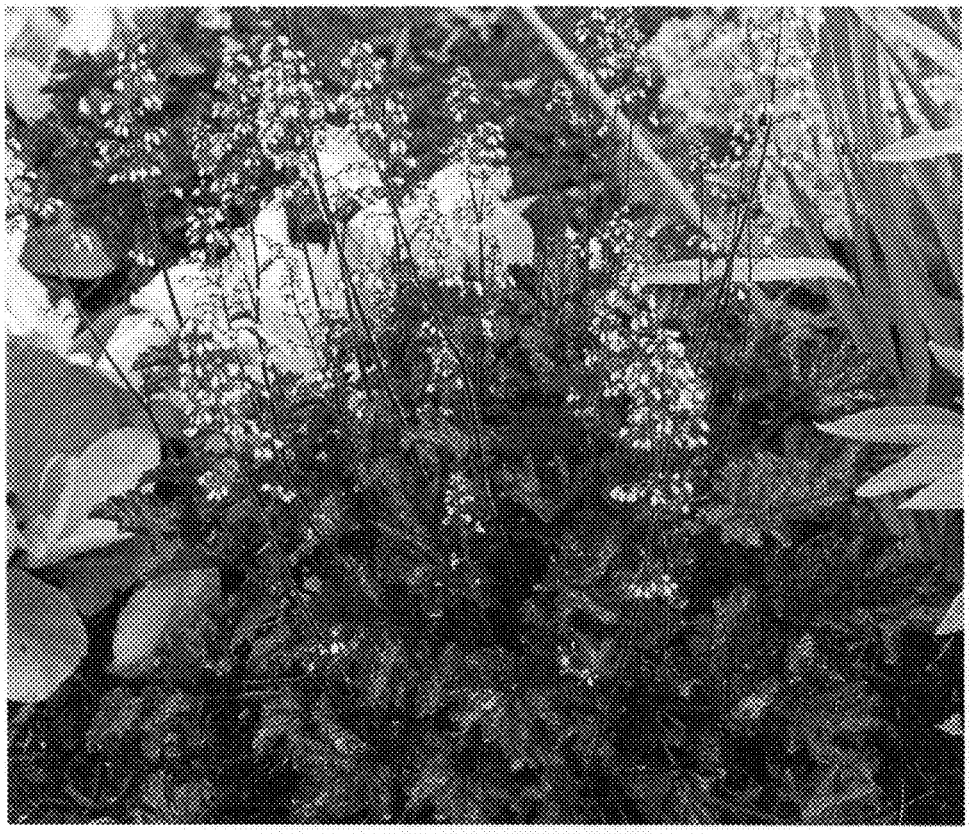
Figure 1 above, Figure 2 below